United States Patent [19]

Wildemeersch

[11] Patent Number: 4,721,105

[45] Date of Patent: Jan. 26, 1988

[54] DEVICE FOR FIXING AN INTRA-UTERINE CONTRACEPTIVE DEVICE TO THE UTERINE WALL

[76] Inventor: Dirk Wildemeersch, Vossenhul 8, Knokke-Heist, Belgium, 8300

[21] Appl. No.: 714,704

[22] Filed: Mar. 21, 1985

[30] Foreign Application Priority Data

Mar. 29, 1984 [BE] Belgium ................ 212661

[51] Int. Cl.$^4$ ............................................ A61F 5/46
[52] U.S. Cl. ...................................................... 128/130
[58] Field of Search ............... 128/127, 128, 129, 130, 128/131; 604/11, 15, 16, 17, 18, 891

[56] References Cited

U.S. PATENT DOCUMENTS

| | | | |
|---|---|---|---|
| 3,410,265 | 11/1968 | Chaft | 128/130 |
| 3,515,132 | 6/1970 | McKnight | 128/130 |
| 3,598,115 | 8/1971 | Horne, Jr. | 128/130 |
| 3,675,639 | 7/1972 | Cimber | 128/130 X |
| 3,840,005 | 10/1974 | Walker | 128/130 |
| 3,848,590 | 11/1974 | Kitrilakis | 128/129 |
| 3,867,933 | 2/1975 | Kitrilakis | 128/129 |
| 3,954,103 | 5/1976 | Garcia-Roel et al. | 128/130 |
| 4,022,198 | 5/1977 | Johnson | 128/130 |
| 4,026,281 | 5/1977 | Mayberry et al. | 128/130 |
| 4,094,313 | 6/1978 | Komamura et al. | 128/130 |
| 4,194,503 | 3/1980 | Csatary | 128/130 |
| 4,249,531 | 2/1981 | Heller et al. | 604/891 |

Primary Examiner—Richard T. Stouffer
Attorney, Agent, or Firm—Weingarten, Schurgin, Gagnebin & Hayes

[57] ABSTRACT

The present invention relates to a device for the insertion and fixation of an intrauterine contraceptive devide (IUD) to the uterine fundus of a female in the immediate post-partum or post-abortal period. The device comprises a thread affixed to the IUD and to a retaining member, a needle for the insertion of the retaining member attached to the thread into the uterine muscle, a protecting member for the needle, a receiving member for the IUD, an actuating member for the needle, movable with respect to the protecting member, and a locking member for temporarily locking the actuating member to the protecting member. This device extends backwards to form a gripping member, while the retaining member loosely engages the needle and an element for achieving and maintaining a traction on the thread, ensuring the cooperation of the retaining member with the needle was long as the locking member and the protecting member are not disengaged and the IUD is not released from its receiving member.

20 Claims, 13 Drawing Figures

DEVICE FOR FIXING AN INTRA-UTERINE CONTRACEPTIVE DEVICE TO THE UTERINE WALL

FIELD AND BACKGROUND OF THE INVENTION

The present invention relates to a device for the insertion and fixation of an intrauterine contraceptive device (IUD) to the uterine fundus of a female in the immediate post-partum or post-abortal period.

For many years, numerous studies have been done on the possibility of immediate post-partum insertion of IUDs. This method offers many advantages, especially in the developing world which faces overpopulation. The method of immediate post-partum insertion is of high interest in these countries because a high proportion of pregnant women deliver in a hospital setting mostly on an out-patient basis. So, the method reaches a large number of motivated women, confers protection before resumption of sexual activity and ovulation, is easily inserted without the slightest pain, does not interfere with lactation and the financial burden is small.

Unfortunately, the few reported experiences of immediate post-partum insertion, in which several models of IUDs have been used, lead to rather disappointing results because of a high rate of expulsion mainly during the first three months. The rate of translocation after insertion of the IUD has not been mentioned in these studies, but is most probably higher than the expulsion rate. Translocation of an IUD not only hinders its efficiency but can also damage the uterus, and thus be dangerous for the health of the woman.

A method of fixing the IUD in the uterine wall has been proposed in two patents namely in U.S. Pat. No. 3,598,115 and U.S. Pat. No. 3,954,103.

The first of these documents, U.S. Pat. No. 3,598,115, discloses a conventional device for the insertion of a special IUD into the uterine cavity. The IUD is provided with a retaining member, which is of sufficient rigidity to penetrate the uterine muscle under the action exerted on the back portion of the IUD. Such a rigid connection between the IUD and its retaining member is not desired because slight translocations of the IUD could harm the uterine wall and cause bleeding and pain. On the other hand, problems may also result during the involution of the post-partum uterus when the IUD has not been affixed in the central part of the uterine fundus.

The second document U.S. Pat. No. 3,954,103 and corresponding West German Pat. No. DE-2,505,941, describes an apparatus for the insertion and fixation of an IUD in the post-partum uterus, which is provided with a thread and a hook for the fixation of the IUD in the uterine wall.

This device consists of an outer cylindrical guide and an inner cylindrical member provided, on its front portion, with a needle on which a removable hook is attached. The IUD is placed between the outer and the inner cylinders. Outer and inner cylinders are temporarily interlocked. The needle and hook, attached to the inner cylinder, is partially covered by the outer cylinder.

The inner cylindrical member fits on the surgeon's finger for manual insertion into the uterus. The unlocking of the two cylinders is assured by manual force as the guide frontal portion engages the uterine wall. This manoeuvre is followed by the penetration of te needle in the uterine muscle. The needle and cylindrical members are then removed, leaving the hook, affixed to the IUD by a strap, in place.

This device is unpractical in use, due to the need for the introduction of the surgeon's finger or hand in the uterine cavity. This not only causes discomfort to the patient, but most of all this manoeuvre becomes almost impossible when the uterus is well contracted, which needed for an appropriate fixation of the retaining member in the wall of the uterine fundus. Moreover, insertion after abortion is impossible due to the too large diameter of the instrument. Also, no means have been provided for avoiding accidental disengagement of the retaining member from the needle before penetration of the needle in the uterine muscle, in which case the utility of the intervention would be completely lost. Finally, the traction of the thread ensures the extraction of the IUD from the device. This force could cause the retaining hook to be pulled out the uterine muscle.

SUMMARY OF THE INVENTION

The aim of the present invention is to provide a device for easy and correct insertion of an IUD in the uterine cavity, and its fixation in the muscular wall of the uterine fundus. The purpose of the invention is to make the fixation possible in the immediate post-partum period as well as in the immediate post-abortal period. The device of the invention avoids the above mentioned inconveniences with the devices of the prior art. The IUD remains affixed in the uterine wall at least until the uterus has returned to its normal size, but nothing opposes the IUD being affixed for longer periods of time.

These goals are reached when a device for the insertion and the fixation of an intrauterine contraceptive device (IUD) to the uterine fundus of a female in the immediate post-partum or post-abortal period is provided, which comprises:

a thread affixed to the IUD and to a retaining member a needle for the insertion of the retaining member attached to the thread into the uterine muscle, a protecting member for the needle, a receiving member for the IUD an actuating member for the needle, movable with respect to the protecting member, means for temporarily locking the actuating member with regard to the protecting member, in which the device extends backwards to form a gripping member the retaining member loosely engages the needle means are provided for achieving and maintaining a traction on the thread, ensuring the cooperation of the retaining member with the needle as long as the means for locking the actuating member with regard to the protecting member are not disengaged and the IUD is not released from its receiving member Another object of the invention is to provide a device in which:

the means for locking the actuating member with respect to the protecting member are means which are controlled independently of any displacement of the members which they lock, the control mechanism of the locking means is provided on the gripping member stop means are provided for limiting the penetration depth of the needle into the uterine muscle.

According to another characteristic feature of the invention, the portion of the thread to be inserted into the uterine wall is provided with a deformation which forms the retaining member, whereby the thread is retained by the uterine muscle.

According to an additional characteristic feature of the invention, the deformation is a knot in the thread.

Still another characteristic feature of the invention is that the needle is a needle provided with a sharp edge and a slot for receiving a loop of the thread.

According to another characteristic feature of the invention, the needle is a hollow needle provided with a sharp edge, and the thread is provided with a pin to be inserted in the lumen of the needle.

According to yet another characteristic feature of the invention, the needle is a hollow needle without sharp edge at forwards end, and the thread is provided with a deformation comprising on one side a pin to be inserted in the canal of the nedle, and on the other side a point, to ensure the penetration of the thread, pushed by the needle, into the uterine muscle.

According to a characteristic feature of the invention, the thread and the retaining member are made of a biologically inert material.

According to another characteristic feature of the invention, the thread and the retaining member are made of a bio-degradable material.

Another object of the invention is to provide a device which consists of:

a needle, provided at the front end of a stem which serves as actuating member and which enlarges at its rear end in a thumb-piece a tubular protecting member, the dimensions of which are sufficient for making holding member for the IUD means for temporarily locking the protecting member with respect to the actuating member in a position in which the front end of the needle is at most flush with the front end of the protecting member retractable stop means for allowing in a first step a limited movement of the protecting member with regard to the needle, and thus a limited penetration of the needle into the uterine muscle, then further backward withdrawal of the protecting member, releasing the IUD while the thread is kept maintained in the uterine muscle by the needle.

According to another characteristic feature of the invention, temporary locking of the protecting member with regard to the actuating member is obtained by locking these members by a pin extending through bores in the actuating member and the protecting member.

According to a further characteristic feature, the actuating member is provided with a second bore, receiving a pin which, when the protecting member is interlocked with the actuating member, is located at a distance from the rear end of the protecting member which corresponds with the desired penetration depth of the needle in the uterine muscle, and said second bore is located at a distance from the enlarged part of the actuating member which makes the thumb-piece, which corresponds at least to the travel of the protecting member necessary for releasing the IUD.

According to another characteristic feature of the invention, the protecting member is a tubular member of restricted length, integral with two legs connected to a collar sliding on the actuating member, and the locking of the protecting member is obtained through retactable pins provided in the actuating member, acting on the collar.

Another object of the invention is to provide a device which has a needle, an actuating member, the drawer-like front part of which is intended to receive the IUD, and the rear part of which enlarges to form a thumb-piece, a protecting member which makes a guide, in which slides the actuating member with the needle, the needle being secured to the drawer-like front part of the actuating member and cooperating with a thread secured to the IUD which is kept in the drawer-like front part of the actuating member, means being provided for ensuring the temporary locking of the protecting member with respect to the actuating member, for limiting the penetration depth of the needle in the uterine muscle, and also for ensuring expulsion of the IUD kept in the drawer-like front part of the actuating member.

According to a characteristic feature of the invention, the length of the needle is limited to the desired penetration depth of the needle in the uterine muscle, and the drawer-like front part of the actuating member makes a stop unit which limits the penetration depth of the needle into the uterine muscle, by abutting against the uterine fundus.

According to another characteristic feature of the invention, the expulsion of the IUD is obtained through a flange, provided in the bottom of the protecting member at the front part of the drawer-like member, whereby this flange cooperates with the thread in order to expel the IUD while the actuating member is moved forward with respect to the protecting member, which movement causes the penetration of the needle with the thread into the uterine muscle.

According to still another characteristic feature of the invention, the temporary interlocking of the protecting member and the actuating member is ensured by the resilient engagement of a detent on the actuating member into a recess in the protecting member.

Another object of the invention is to provide a device which has a tubular protecting member, provided with two slots at its front end, for receiving the legs of a IUD, and with a stop and a slot at its rear end, the protecting member ending in a handle, and a tubular actuating member, received in the protecting member in abutment with the stop, the tubular actuating member being secured at its front end to a needle and at its rear end to a thumb-piece cooperating with the slot in the protecting member, the IUD being affixed to a thread provided with a retaining member cooperating with the needle, and to an extraction thread which makes, by passage and traction through the actuating and protecting members, means for securing the thread to the needle and means for locking the IUD in the slots and the actuating member in the protecting member.

According to another characteristic feature of the invention, the distance between the bottom of the slots and the stop is at most equal to the longitudinal distance between the legs of the IUD, when the thread is tightly engaged with the needle, and the rear end of the actuating member.

According to a further characteristic feature of the invention, the bottom of the slot makes, through cooperation with the thumb-piece, a stop limiting the penetration of the needle in the uterine muscle.

DESCRIPTION OF THE DRAWING

These and other characteristics of the invention will be more readily understood when refering to the description as well as to the accompanying drawings which represent, merely by the way of examples, some embodiments of the invention, and in which.

DETAILED DESCRIPTION

Figure 1:
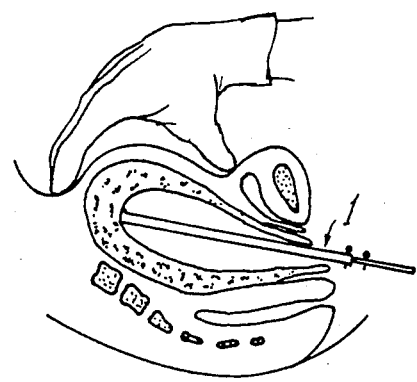
FIG. 1 represents schematically the procedure of immediate post-partum insertion of an IUD when using a device according to the invention.

Referring now to the drawings, and more particularly to FIG. 1 which shows, merely as an example, one way of use of a device according to the invention for the insertion and the fixation of an IUD into the uterine muscle in the immediate post-partum period, manual pressure is applied on the uterine fundus in order to bring the uterine cervix as far as possible down into the vagina, and the device is inserted in the uterine cavity through the dilated cervix until its front portion abuts the uterine fundus.

Figure 8:
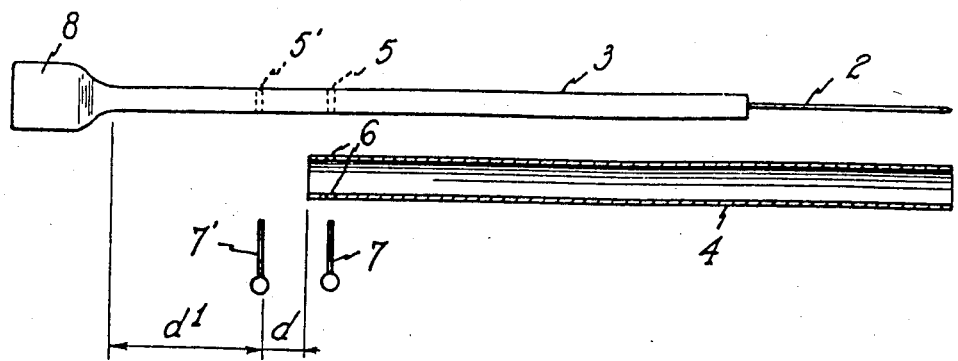
FIG. 8 is an exploded view of the various elements of an embodiment of a device for the insertion and the fixation of an IUD to the uterine fundus according to the invention.

The device 1 shown in FIG. 1, which represents one embodiment of a device according to the invention, is shown more in detailed, though schematically and with the exclusion of the IUD and thread affixed thereto, in FIG. 8.

According to the embodiment illustrated in FIG. 8, the device is essentially made of a needle 2, fitted at the fore end of a stem acting as an actuating member 3, and a tubular protecting member (shown in cross section). Bores 5, 5' are formed in the actuating member 3, and diametrically opposed bores 6 are provided in the wall of the tubular protecting member 4. Pins 7, 7' are provided for insertion into said bores 5, 5' and 6.

Figure 2:
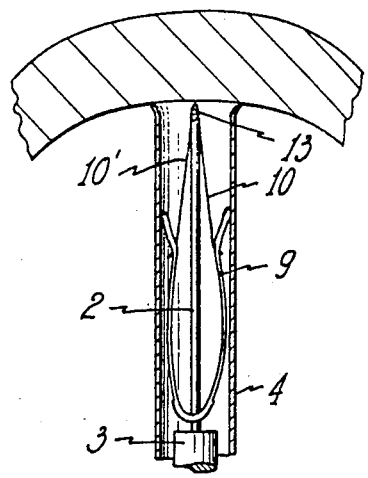
FIGS. 2, 3 and 4 represent the several steps of insertion and fixation of an IUD in the wall of the uterine fundus, using a device according to the invention.
Figure 3:
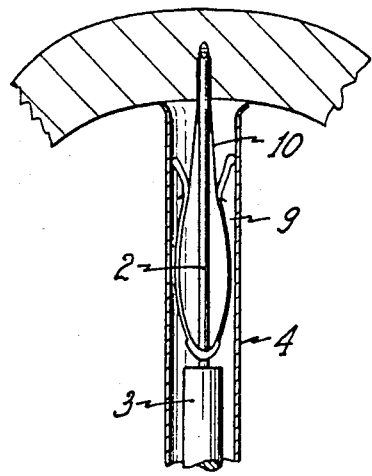
Figure 4:
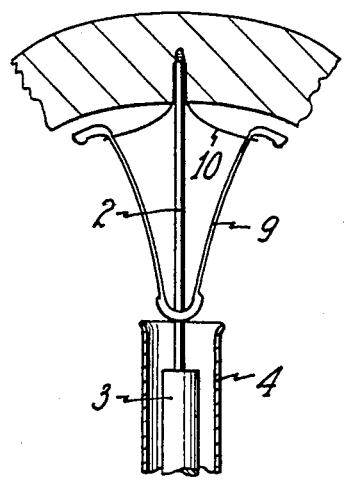

The bore 5 in the actuating member 3 and the bores 6 in the protecting member 4 are provided to allow, when cooperating with the pin 7, the locking of the actuating member 3 with respect to the protecting member 4, when the needle 2 and the actuating member 3 are inserted into the protecting member 4 as shown partially and at a larger scale in FIGS. 2 to 4. In this position, the fore part of the needle is flush with the fore part of the protecting member as shown in FIG. 2.

The bore 5' is formed in the actuating member 3, at such a location that, when inserted in the bore 5', the pin 7' is positioned at a distance d from the rear end of the protecting member 4, interlocked with the actuating member 3 through the pin 7, which corresponds to the penetration depth of the needle with the thread in the uterine muscle.

According to the embodiment shown in FIG. 8, the rear end of the actuating member 8 is made as a thumb-piece 8.

The bore 5' is a distance $d^1$ away from the enlarged part of the thumb-piece 8.

The operation of the device according to the invention, when applied to this particular embodiment, will be explained more in details with reference to FIGS. 2 to 4.

In use of the device of the invention, an IUD as schematically shown in 9 is attached to a thread 10 provided with a retaining member to be inserted in the uterine muscle. Although the IUD shown in the drawing is V-shaped, any other type of IUD may obviously be used with a device according to the invention. The thread 10 is attached to the needle, and the IUD 9, affixed to the thread 10, is inserted while collapsed through the rear end of the protecting member, and pushed forward therein.

The protecting member 4, against the inner wall of which the collapsed IUD rubs, holds said IUD in a collapsed position and ensures the tightening of the thread by which the IUD is attached to the needle. This tightening reliably holds the attachment of the thread 10 to the needle 2.

When the bores 6 in the protecting member 4 are in register with the bore 5 in the actuating member 3, the pin 7 is passed through the bores 5 and 6, thereby interlocking the actuating member 3 with the protecting member 4. As mentioned before, in this position, the front end of the needle 2 is flush with the front end of the protecting member 4. The device is now ready to be used as shown in FIG. 1.

The apparatus is inserted in the uterus until its front end abuts the uterine wall in the central part of the fundus as shown in FIGS. 1 and 2. As can be seen more clearly in FIG. 2, the large front end of the protecting member can be brought into contact with the uterine wall without any risk of damage to the wall.

Pin 7 is taken away while pin 7' remains in bore 5'.

The actuating member 3 is then pushed in the direction of the uterine fundus. The protecting member, which is now loose with respect to te actuating member 3, moves backwards over the actuating member 3, and at the same time the needle 2, to which the thread 10 is attached, penetrates the uterine muscle in the fundus. The penetration depth is controlled by the protecting member 4 which cannot move further backward than pin 7'. The protecting member 4 has thus moved backwards over a distance d while the needle 2 has penetrated the uterine muscle over the same distance, and the IUD, which has been pulled forward by thread 10, has also moved forward over the same distance in the protecting member 4. The device is then in the position as illustrated in FIG. 3.

The pin 7' is then taken away, and the protecting member 4 is moved backwards. This manipulation is done without pushing the actuating member 3 in the direction of the uterine fundus. The backward displacement of the protecting member 4 is continued over a distance $d^1$ which must be at least equal to the distance necessary for ensuring the complete liberation of the IUD 9 from the protecting member 4 as illustrated in FIG. 4. During the backward movement of the protecting member 4, the actuating member 3 is kept steady in order to avoid the thread 10 being pulled out of the uterine wall due to rubbing of the protecting member 4 on the IUD.

When the protecting member is completely withdrawn, the entire device is taken out the uterus, while the thread, fixed to the IUD, is retained in the uterine muscle by the retaining member, in this case loop 10′ of thread 10. In order to avoid misplacement of the IUD in the uterine cavity, the length of the thread 10 is such that after being inserted in the uterine muscle, no substantial displacement of the IUD from its original position is possible.

The slack in the thread is however sufficient to allow the IUD, if the thread has not been inserted exactly in the central part of the uterine fundus, to recenter itself within the uterine cavity when returned to its normal dimensions, without the risk of inducing high tension on the thread fixed in the uterine muscle.

Figure 5:
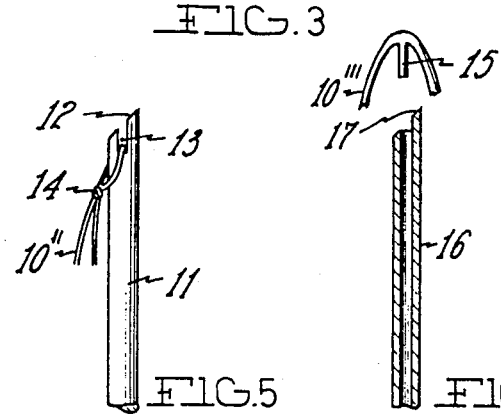
FIGS. 5, 6 and 7 represent different embodiments of needles and threads associated with these needles.

In the embodiment shown in FIGS. 2 to 4, a needle 11 is provided with a sharp edge 12 and an axial slot 13, as shown on enlarged scale in FIG. 5. In this embodiment of FIGS. 2 to 4, the thread 10 forms a loop 10′, by being attached to both legs of the IUD, and the loop 10′, which forms the retaining member, engages with slot 13 of needle 11.

In order to improve retention of the thread in the uterine muscle, one can also foresee to make in the thread a deformation, acting as retaining member. One of the more simple solutions is to make a knot 14 in the thread, and to use the needle as illustrated in FIG. 5 to insert the thread with the knot in the uterine muscle.

Figure 6:
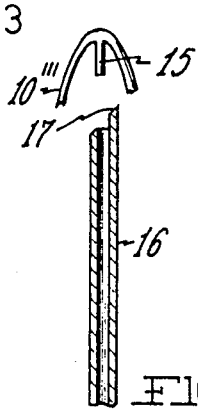
Figure 7:
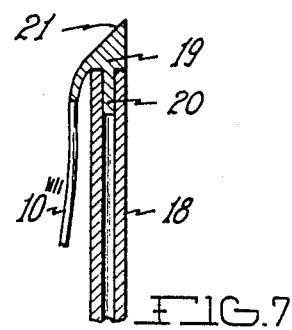

Another solution, to be used with a monofilament thread, is to form a pin 15 in the thread, and to utilize a hollow needle 16 provided with a sharp edge 17. This pin 15, loosely inserted in the lumen of the needle 16, ensures the retention of the thread 10′′′ on the needle under the effect of the tension exerted on the thread. The disengagement of the thread from the needle is achieved by simple withdrawl of the needle, without any effort being exerted on the thread. This solution is shown in FIG. 6 where, for the sake of clarity, the needle is shown in side view, and the thread in front view.

Yet another solution resides in using a hollow needle 18 without sharp edge, and to make a deformation in the thread consisting at one end of a pin 20 for its loose fixation in the needle, and at the other end a point 21 for penetration into the uterine muscle under the pulling action exerted by the needle 18. After withdrawl of the needle, deformation 19 disengaging from the needle by simple slipping off, retains the thread in the uterine muscle.

These various solutions are of course given merely by way of example, and other ways for loosely fixing the thread to the needle, which all are included in the scope of the invention, will be evident for the man of the art.

Figure 9:
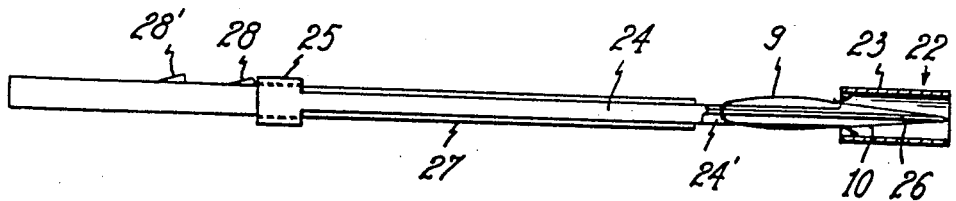
FIG. 9 is a side view of another embodiment of a device according the invention.

Another embodiment of the invention is illustrated in FIG. 9.

According to this embodiment, the protecting and keeping member 22 for the IUD is made in the form of a short tubular member 23, from which extend two legs 24, 24′, which themselves are made integral with a collar 25. The device has also a needle 26 and an actuating member 27 attached to the needle. The actuating member 27 has two resiliently collapsible stops 28, 28′, spaced from each other by a distance corresponding to the distance d in FIG. 8.

The operation of the device is substantially the same as the operation of the one illustrated in FIG. 8. However, as the collar 25 comes merely in abutment with the stop 28, without being actually interlocked with the actuating member 27, care must be taken not to push the collar 25 forward with respect to the actuating member 27 while handling the device. Such a forward movement could indeed cause the disengagement of the thread 10 from the needle 26 already before the letter has penetrated the uterine muscle.

Figure 10:
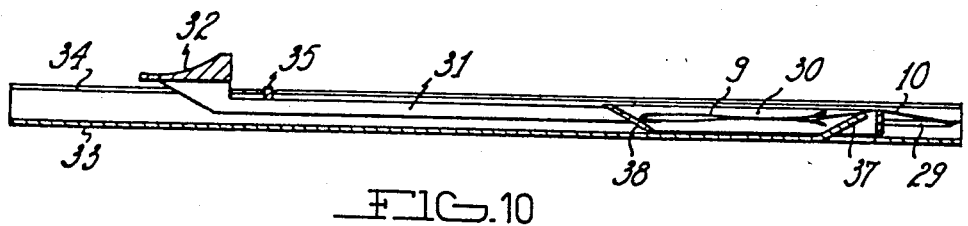
FIG. 10 is a side cross-sectional view, along line A—A in FIG. 11, of another embodiment of a device according to the invention
Figure 11:
FIG. 11 is a top view of the device of FIG. 10, FIGS. 12 and 13 are cross-sectional top and side views of another simplified embodiment of a device according to the invention.

FIGS. 10 and 11 show respectively in cross sectional side view and in top view another embodiment of a device according to the invention.

According to this embodiment, the device has a needle 29, fixed to the drawer-like front end 30 of an actuating member 31, which ends, at its rear end, in a thumb-piece 32.

The actuating member 31 slides into a hollow guide 33, provided with a longitudinal slot 34, such guide acting as protecting member.

Actuating member 31 is made integral with a detent 35 adapted for cooperation with a recess 36 formed on each side of the slot 34.

The bottom of the protecting member 33 has a slantwise deformation 37, located in the front of the drawer-like member when the detent 35 engages the recess 36. The rear end of the drawer-like member is also provided with a oblique wall 38.

In use, the IUD 9 is in a jammed position between the lateral walls of the drawer-like member, while the width between these walls substantially corresponds with the width of slot 34, and the thread 10 is tightly interconnected with the needle 29. In this position, the detent 35 engages the recess 36, and the front end of the needle is at most flush with the front end of the protecting member 33.

The device in this condition, is inserted into the uterine cavity and brought into contact with the uterine fundus.

The thumb-piece 32 is then pressed downward and pushed forward. By this way, detent 35 is first disengaged from recess 36, and thereafter the actuating member 31 with the needle 29 is moved forward within the protecting member 33.

By this way, the needle 29 protrudes from the protecting member 33 and penetrates the uterine muscle, carrying along the thread 10. At the same time, the IUD 9 is carried by the drawer-like member until it comes into contact with the slantwise deformation or flange 37. Since the IUD 9 is mainly kept fixed in the front part of the drawer-like member, the flange 37 causes rise of the IUD along the flange and at the same time moves it back in the drawer-like member 30, in dependency of the tightening and the elasticity if the thread. In order to avoid the back portion of the IUD from getting stuck in the drawer-like member 30, the back part 38 of the drawer-like member is in a backward oblique position. Cooperation of the thread 10, which avoids substantial backward movement of the IUD in the drawer-like member, with the flange 37, and the forward movement of the drawer-like member 30, will compel the IUD to climb along the flange 37 up to being expelled through slot 34.

Release of the IUD can be completed without risks before the thread has been completely inserted into the uterine muscle. Indeed, right from the begining of the penetration of the needle and thread into the uterine muscle, the thread is kept fixed to the needle by the uterine tissue.

According to this embodiment, the length of the needle 29 corresponds to the desired depth of penetration in the uterine tissue, and the front end of the drawer-like member 30 acts as a stop which limits the penetration of the needle 29 in the uterine muscle.

Figure 12:
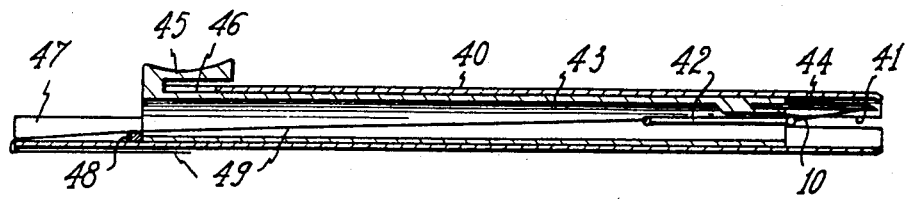
Figure 13:
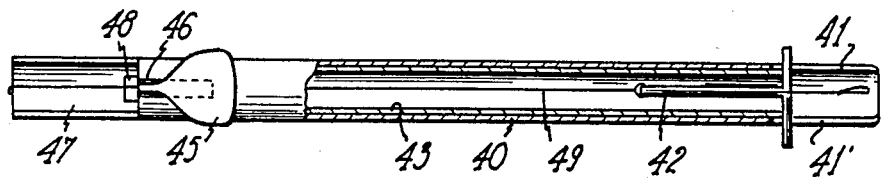

Referring now to the embodiment illustrated in FIGS. 12 and 13, the device is made of a tubular protecting member 40 provided at its front end with slots 41,41′ for receiving the legs of an IUD 42, and of an actuating member, also generally tubular, with a needle 44 at its front end, which needle cooperates with a thread 10 fixed to the IUD 42.

The actuating member is made integral, at its rear end, with a thumb-piece 45 which runs in a longitudinal slot 46 made in the protecting member 40.

The protecting member 40 is connected at its rear end to a handle 47 which makes a gripping member with the rear part of the protecting member.

A stop 48 is formed at the rear end of the protecting member 40, for cooperation with the rear part of the actuating member 43.

A thread 49 is fixed at the rear end of the IUD, which forms an extraction thread in order to make the extraction of the IUD easier when the IUD has to be withdrawn from the uterine cavity. By way of example, the IUD is "T-shaped".

According to this embodiment, the locking member for the actuating member 43 is the thread 49 which extends through the protecting member 40 and the actuating member 43 leaves the protecting member 40 at its rear end, is held fixed to it, and keeps the actuating member against the stop 48.

For that purpose, the distance between the rear end of the slots 41, 41′ and the stop 48 is at the most equal to the longitudinal distance between the two legs of the IUD, when thread 10 is tightened on the needle 44, and the rear end of the actuating member 43. In this way, backward traction on the thread 49 ensures the abutment of the actuating member 43 against the stop 48 on the protecting member 40, the IUD being positioned between thread 49 and thread 10 which is fixed to the needle. This traction reliably keeps the IUD in place in the protecting member 40, and also keeps the thread 10 fixed to the needle 44.

The traction of thread 49 is maintained by bending and holding the thread on the external part of the rear end of the protecting member 40 or of the handle 47.

In use, the device is inserted into the uterus until the rounded off front end of the protecting member 40 comes in contact with the uterine fundus. The thumb-piece 45 is then pushed forward while the thread 49 is released. This action causes the forward movement of the actuating member 43 as well as the penetration of the needle 44, to which the thread 10 is fixed, in the uterine muscle.

Release of thread 49 ensures the release of the IUD 42, the legs of which can in this way move freely in the slots 41, 41′. In this way, the device can be withdrawn from the uterine cavity, while the IUD remains reliably fixed in the uterine muscle.

According to a preferred embodiment of the invention, the end of the slot 46 serves as a stop for limiting the forward movement of the actuating member 43, and thus the penetration depth of the needle in the uterine wall.

The invention has been described and illustrated merely by way of example and in no way restrictive. Numerous changes in its construction may be made without departing from the spirit of the invention.

What is claimed is:

1. For use with an intrauterine contraceptive device (IUD), a device for insertion and fixation of the IUD to the uterine fundus of a female in the immediate post-partum or post-abortal period, which comprises:
   a thread (10) affixable to the IUD (9; 40) and affixed to a retaining member (10′; 14; 15; 19),
   a needle (2; 26; 29; 44) for the insertion of the retaining member (10′; 14; 15; 19) affixed to the thread into the uterine muscle,
   a protecting member (4; 22; 33; 40) for the needle including
   a receiving member (4; 22; 30; 41, 41′) for the IUD,
   an actuating member (3; 27; 31; 43) for the needle, movable with respect to the receiving member,
   means (5,6,7; 25,28; 35,36; 48,49) for temporarily locking the actuating member with respect to the receiving member,
   wherein
   the device extends backwards to form a gripping member (8; 25,27; 32,33; 47,45),
   the retaining member (10′; 14; 15; 19) loosely engages the needle (2; 26; 29; 44),
   means (4; 22; 30; 49) are provided for achieving and maintaining a traction on the thread (10), said traction means adapted to ensure the cooperation of the retaining member (10′; 14; 15; 19) with the needle (2; 26; 29; 44) as long as the means (5,6,7; 25,28; 35,36; 48,49) for locking the actuating member with regard to the protecting member are not disengaged and the IUD is not released from its receiving member (4; 22; 30; 41,41′).

2. A device according to claim 1, wherein
   the means for locking (5,6,7; 25,28; 35,36; 48,49) the actuating member with respect to the receiving member are means which are controlled independently of any displacement of the members (3,4; 22,27; 31,33; 40,43) which they lock, including
   a control mechanism provided on the gripping member, and
   stop means (7′; 28′; 30; 46) provided for limiting the penetration depth of the needle into the uterine muscle.

3. A device according to claim 2 wherein the portion of the thread to be inserted into the uterine wall is provided with a deformation (14; 15; 19) which forms the retaining member, whereby the thread is adapted to be retained by the uterine muscle.

4. A device according to claim 3, wherein the deformation is a knot (14) in the thread.

5. A device according to claim 4, wherein the needle (2; 26; 29) is a needle (11) provided with a sharp edge (12) and a slot (13) for receiving a loop of the thread (10).

6. A device according to claim 2, characterized in that the needle (2; 26; 29) is a hollow needle (16) provided with a sharp edge (12), and the thread (10) is provided with a pin (15) to be inserted in the lumen of the needle.

7. A device according to claim 2, characterized in that the needle (2; 26; 29) is a hollow needle (18) without any sharp edge at its forward end, and the thread (10) is provided with a deformation (19) comprising at one end a pin (20) to be inserted in the canal of the needle, and at the other end a point (21), to ensure the penetration of the thread, pushed by the needle, into the uterine muscle.

8. A device according to claim 2, wherein the thread (10) and the retaining member (10′; 14; 15; 19) are made of a biologically inert material.

9. A device according to claim 2, wherein the thread (10) and the retaining member (10'; 14; 15; 19) are made of a bio-degradable material.

10. A device according to claim 2, characterized by said needle (2; 26), provided at the front end of a stem, said stem serving as said actuating member (3; 27), said stem being enlarged at its rear end to form said gripping member (8), said protecting member (4; 22) being tubular with dimensions which are sufficient to make it a holding member for the IUD (9)

said means (5,6,7; 28) for temporarily locking the actuating member with respect to the receiving member being in a position in which the front end of the needle is at most flush with the front end of the protecting member (4; 22), said stop means (5',7'; 28') being retractable for allowing in a first step a limited movement of the protecting member with respect to the needle, and thus a limited penetration of the needle into the uterine muscle, then further backward withdrawal of the protecting member, releasing the IUD while the thread is kept maintained in the uterine muscle by the needle.

11. A device according to claim 10, characterized in that said means for temporarily locking the actuating member (4) with respect to the receiving member is obtained by locking these members by a pin (7) extending through bores (5,6) in the actuating member (3) and the receiving member (4).

12. A device according to claim 11, characterized in that the actuating member (3) is provided with a second bore (5'), receiving a pin (7') which, when the receiving member is interlocked with the actuating member, is located at a distance from the rear end of the receiving member which corresponds with the desired penetration depth of the needle in the uterine muscle, and in that said second bore is located at a distance from the enlarged part of the actuating member, which makes the gripping member which corresponds at least to the travel of the receiving member necessary for releasing the IUD.

13. A device according to claim 10, characterized in that the receiving member (22) is a tubular member (23) of restricted length, integral with two legs (24,24') connected to a collar (25) sliding on the actuating member (27), and in that the locking of the receiving member (22) is obtained through retractable pins (28,28') provided in the actuating member, acting on the collar (25).

14. A device according to claim 2, characterized by said actuating member (31) being provided with a front part in the form of a drawer which is adapted to receive the IUD, and a rear part of which enlarges to form said gripping member (32), said receiving member (33) making a guide, in which slides the actuating member (3) with the needle (29), the needle (29) being secured to the drawer front part (30) of the actuating member (31) and cooperating with said thread (10) when secured to the IUD (9) which is kept in the drawer front part (30) of the actuating member (31), said means for temporarily locking the actuating member with respect to the receiving member adapted to limit the penetration depth of the needle in the uterine muscle, and also to ensure expulsion of the IUD kept in the drawer front part of the actuating member.

15. A device according to claim 14, characterized in that the length of the needle (29) is limited to the desired penetration depth of the needle in the uterine muscle, and in that the drawer front part (30) of the actuating member makes said stop means for limiting the penetration depth of the needle (29) into the uterine muscle, by abutting against the uterine fundus.

16. A device according to claim 15, characterized in that the expulsion of the IUD is obtained through a flange (37), provided in the bottom of the receiving member at the front part of the drawer member, whereby this flange cooperates with the thread in order to expel the IUD (9) while the actuating member (31) is moved forward with respect to the receiving member (33), which movement causes the penetration of the needle (29) with the thread (10) into the uterine muscle.

17. A device according to claim 16, characterized in that said means for temporarily locking includes a detent (35) on the actuating member (31) and a recess (36) in the receiving member (33) which are adapted to resiliently engage each other.

18. For use with an intrauterine contraceptive device (IUD), a device comprising a tubular protecting member (40), provided with two slots (41,41') at its front end, for receiving the legs of an IUD (42), and with a stop (48) and a slot (46) at its rear end, the protecting member (40) ending in a handle (47), and a tubular actuating member (43), received in the protecting member (40) in abutment with the stop, the tubular actuating member (43) being secured at its front end to a needle (44) and at its rear end to a thumb-piece (45) cooperating with the slot (46) in the rear end of the protecting member (40), a first thread (10) provided with a retaining member cooperating with the needle (44), said first thread being affixable to the IUD, and an extraction thread (49) which makes, by passage and traction through the actuating and protecting members, means for securing the first thread (10) to the needle (44) and means for locking the IUD (42) in the slots the actuating member (43) in the protecting member (40). (41,41') at the first end of the protecting member and also in 19. A device according to claim 18, wherein the distance between the bottom of the front end slots (41, 41') and the stop (48) is adapted to be at most equal to the longitudinal distance between the legs of the IUD, when the thread (10) is tightly engaged with the needle, and the rear end of the actuating member (43).

20. A device according to claim 19, wherein the bottom of the front end slot (46) makes, through cooperation with the thumb-piece (45), said stop, said stop adapted to limit the penetration of the needle (44) in the uterine muscle.

* * * * *

UNITED STATES PATENT AND TRADEMARK OFFICE
CERTIFICATE OF CORRECTION

PATENT NO. : 4,721,105

DATED : January 26, 1988

INVENTOR(S) : Dirk Wildemeersch (Page 1 of 2)

It is certified that error appears in the above-identified patent and that said Letters Patent is hereby corrected as shown below:

In the Abstract

2nd line, "devide" should read --device--
    17th line, "was long" should read --as long--

Column 1, line 68, "te needle" should read --the needle--

Column 2, lines 8-9, "which needed" should read --which is needed-- line 19, "out the" should read --out of the--

Column 3, line 19, "nedle," should read --needle,--

Column 3, line 68 and Column 4, line 1, "re-tactable" should read --re-tractable--

Column 4, line 68, "refering" should read --referring--

Column 6, line 5, "in details" should read --in detail--
    line 40, "to te" should read --to the--
    line 67, "out the" should read --out of the--

Column 7, line 33, "withdrawl" should read --withdrawal--
    line 43, "withdrawl" should read --withdrawal--
    line 62, "the device" should read --this device--

Column 8, line 2, "letter" should read --latter--
    line 48, "if the thread." should read --of the thread.--
    line 60, "begining" should read --beginning--

UNITED STATES PATENT AND TRADEMARK OFFICE
CERTIFICATE OF CORRECTION

PATENT NO. : 4,721,105
DATED : January 26, 1988
INVENTOR(S) : Dirk Wildemeersch

It is certified that error appears in the above-identified patent and that said Letters Patent is hereby corrected as shown below:

Column 10, line 18, "47, 45)," should read --47, 40),--

Column 11, line 2, "(10',; 14;" should read --(10'; 14;--

Column 12, lines 45-47, "slots the actuating member (43) in the protecting member (40). (41, 41') at the first end of the protecting member and also in" should read
--slots (41, 41') at the first end of the protecting member and also in the actuating member (43) in the protecting member (40).

line 55, "front end slot (46)" should read --rear end slot (46)--

Signed and Sealed this

Sixth Day of June, 1989

Attest:

DONALD J. QUIGG

Attesting Officer

Commissioner of Patents and Trademarks